United States Patent
Karahashi (10) Patent No.: US 10,111,639 B2
(45) Date of Patent: Oct. 30, 2018

(54) MEDICAL IMAGE DIAGNOSTIC APPARATUS AND MEDICAL IMAGE DIAGNOSTIC METHOD

(71) Applicant: TOSHIBA MEDICAL SYSTEMS CORPORATION, Otawara-Shi (JP)

(72) Inventor: Masahiro Karahashi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 289 days.

(21) Appl. No.: 14/982,751

(22) Filed: Dec. 29, 2015

(65) Prior Publication Data

US 2016/0220216 A1    Aug. 4, 2016

(30) Foreign Application Priority Data

Jan. 30, 2015  (JP) ................................. 2015-016746

(51) Int. Cl.
*A61B 6/04*  (2006.01)
*H05G 1/28*  (2006.01)
(Continued)

(52) U.S. Cl.
CPC .............. *A61B 6/54* (2013.01); *A61B 6/5288* (2013.01); *A61B 6/5294* (2013.01); *A61B 6/541* (2013.01);
(Continued)

(58) Field of Classification Search
CPC .... A61B 6/00; A61B 6/03; A61B 6/04; A61B 6/0457; A61B 6/48; A61B 6/52;
(Continued)

(56) References Cited

U.S. PATENT DOCUMENTS 4,158,138 A * 6/1979 Hellstrom ................ A61B 6/02
378/108
7,382,858 B2 * 6/2008 Gohno .................... A61B 6/032
378/209
(Continued)

FOREIGN PATENT DOCUMENTS

JP    04-336046 A    11/1992
JP    3033679        4/2000
(Continued)

OTHER PUBLICATIONS

Office Action dated Aug. 28, 2018, in corresponding Japanese Patent Application No. 2015-016746; citing documents AO, AP, and AQ; therein, 62 pages.

*Primary Examiner* — Anastasia Midkiff
(74) *Attorney, Agent, or Firm* — Oblon, McClelland, Maier & Neustadt, L.L.P.

(57) ABSTRACT

According to one embodiment, a medical image diagnostic apparatus includes an X-ray tube, a rotor and processing circuitry. The X-ray tube radiates an X-ray. The rotor holds the X-ray tube, and rotates together with the X-ray tube at least any of a first rotation speed used for scanning an object and a second rotation speed lower than the first rotation speed. The processing circuitry acquires information on a waiting time up to timing of exposure by the X-ray tube. The processing circuitry further controls a rotation speed of the rotor during the waiting time in accordance with the information on the waiting time.

14 Claims, 5 Drawing Sheets

(51) Int. Cl.
*H05G 1/38* (2006.01)
*A61B 6/00* (2006.01)
*A61B 6/03* (2006.01)

(52) U.S. Cl.
CPC .............. *A61B 6/542* (2013.01); *H05G 1/28* (2013.01); *A61B 6/035* (2013.01); *A61B 6/0457* (2013.01); *A61B 6/481* (2013.01); *A61B 2560/0266* (2013.01); *H05G 1/38* (2013.01)

(58) Field of Classification Search
CPC ....... A61B 6/5288; A61B 6/5294; A61B 6/54; A61B 6/541; A61B 6/542; A61B 6/545; A61B 6/547; A61B 2560/00; A61B 2560/02; A61B 2560/0204; A61B 2560/0214; A61B 2560/0266; A61B 2560/029; G06T 1/00; G06T 1/0007; G06T 1/0014; G06T 2207/00; G06T 2207/20; G06T 2207/20004; G06T 11/00; G06T 11/003; G06T 11/005; G06T 2211/00; G06T 2211/40; G06T 2211/412; G01T 1/00; G01T 1/02; G01T 7/00; G01T 7/005; H05G 1/00; H05G 1/08; H05G 1/26; H05G 1/28; H05G 1/30; H05G 1/38; H05G 1/40; H05G 1/42; H05G 1/44; H05G 1/46; H05G 1/56; H05G 1/62; G01N 23/00; G01N 23/02; G01N 23/04; G01N 23/046; G01N 23/06; G01N 23/08; G01N 23/083; G01N 2223/00; G01N 2223/30; G01N 2223/303; G01N 2223/304; G01N 2223/306; G01N 2223/40; G01N 2223/419; G01N 2223/425

See application file for complete search history.

(56) References Cited

U.S. PATENT DOCUMENTS

| | | | |
|---|---|---|---|
| 7,406,148 B2* | 7/2008 | Russinger | A61B 6/504 378/15 |
| 7,706,498 B2* | 4/2010 | Imai | A61B 6/027 378/20 |
| 7,983,385 B2* | 7/2011 | Heuscher | A61B 6/032 378/11 |
| 8,705,819 B2* | 4/2014 | Carlsen | A61B 6/032 382/128 |
| 2006/0233296 A1* | 10/2006 | Wakai | A61B 6/032 378/8 |

FOREIGN PATENT DOCUMENTS

| | | |
|---|---|---|
| JP | 3047370 | 5/2000 |
| JP | 3210358 | 9/2001 |
| JP | 3432270 | 8/2003 |
| JP | 3673001 | 7/2005 |
| JP | 2006-512995 A | 4/2006 |
| JP | 2008-264273 A | 11/2008 |
| JP | 2012-217547 | 11/2012 |

* cited by examiner

- TIME REQUIRED FOR TRANSITION FROM vi TO vj: = tij
- TIME REQUIRED FOR DECELERATION FROM vi TO vk AND REACCELERATION TO vj:
  = tikj (k < i AND k < j)

DECELERATION IS POSSIBLE UP TO vk THAT GIVES LONGEST ONE OF REQUIRED TIMES tikj EQUAL TO OR LESS THAN ACQUIRED WAITING TIME T

MEDICAL IMAGE DIAGNOSTIC APPARATUS AND MEDICAL IMAGE DIAGNOSTIC METHOD

CROSS-REFERENCE TO RELATED APPLICATIONS

This application claims the benefit of priority of Japanese Patent Application No. 2015-016746, filed Jan. 30, 2015, the entire contents of which are incorporated herein by reference.

FIELD

Embodiments described herein relate generally to a medical image diagnostic apparatus and a medical image diagnostic method.

BACKGROUND

Medical image diagnostic apparatuses include an apparatus in which an imaging system rotates at a high speed at the time of imaging, such as an X-ray computed tomography (CT) apparatus. In the medical image diagnostic apparatus of this type, the imaging system keeps rotating even in a scan waiting time, and electric power is wastefully consumed in some cases. For example, a conceivable method for reducing such power consumption includes: determining that the apparatus is in the scan waiting time, in response to that a top plate has moved to a prescribed position; and ending current application to each unit including a rotation controller.

In a case of ending the current application to each unit, however, rotations of the imaging system are also stopped. Hence, before a rotation speed of the imaging system is regained in order to restart imaging, both the time to start rotations from a rotation stop state and the time to control the rotation speed are necessary, so that an enormous amount of time is required.

The present invention has an object to provide a medical image diagnostic apparatus and a medical image diagnostic method capable of reducing electric power consumed in a scan waiting time and regaining a rotation speed of an imaging system in a short time.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of a medical image diagnostic apparatus and a medical image diagnostic method according to embodiments of the present invention with reference to the drawings.

In general, according to one embodiment, a medical image diagnostic apparatus includes an X-ray tube, a rotor and processing circuitry. The X-ray tube radiates an X-ray. The rotor holds the X-ray tube, and rotates together with the X-ray tube at least any of a first rotation speed used for scanning an object and a second rotation speed lower than the first rotation speed. The processing circuitry acquires information on a waiting time up to timing of exposure by the X-ray tube. The processing circuitry further controls a rotation speed of the rotor during the waiting time in accordance with the information on the waiting time.

Figure 1:
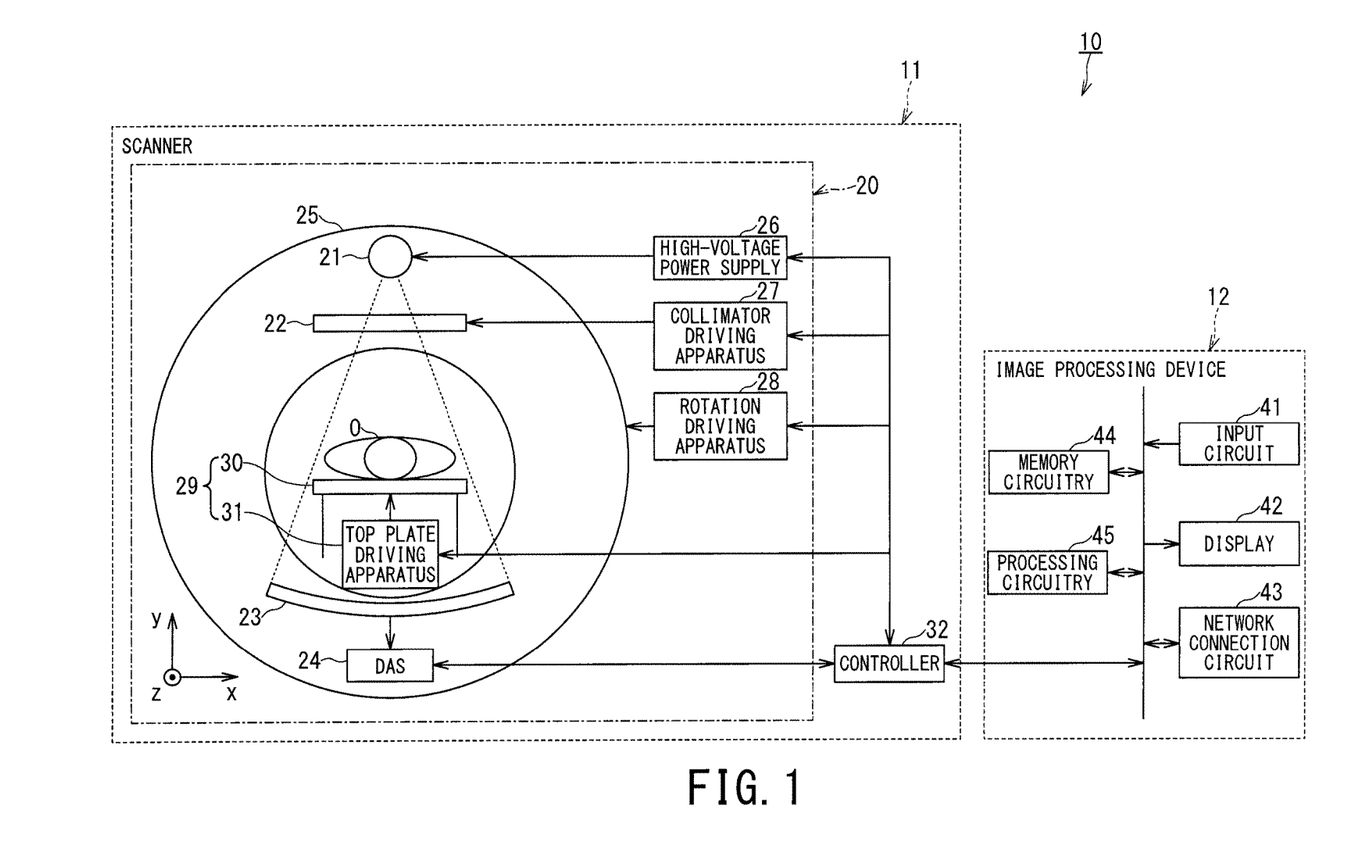
FIG. 1 is a block diagram illustrating a configuration example of a medical image diagnostic apparatus according to an embodiment of the present invention.

FIG. 1 is a block diagram illustrating a configuration example of a medical image diagnostic apparatus 10 according to an embodiment of the present invention.

A modality including a rotation mechanism for an imaging system can be used as the medical image diagnostic apparatus 10, and, for example, a photon counting X-ray CT apparatus and an energy integrating X-ray CT apparatus can be used thereas. In the following description, discussed is an example case where the energy integrating X-ray CT apparatus is used.

The X-ray CT apparatus as the medical image diagnostic apparatus 10 according to the embodiment of the present invention may be of various types such as: a ROTATE/ROTATE type in which an X-ray tube and an X-ray detector integrally rotate around an object; and a STATIONARY/ROTATE type in which a large number of detecting elements are arrayed in a ring-like shape and only an X-ray tube rotates around an object. The present invention can be applied to any of the types. The following description, the ROTATE/ROTATE type is discussed.

In recent years, a so-called multi-tube X-ray CT apparatus in which a plurality of pairs of an X-ray tube and an X-ray detector are mounted on a rotating ring is increasingly commercialized, and development in peripheral technology thereof is advancing. The medical image diagnostic apparatus 10 according to the present embodiment can be applied to both a single-tube X-ray CT apparatus and the multi-tube X-ray CT apparatus. Here, the single-tube X-ray CT apparatus is discussed.

As illustrated in FIG. 1, the medical image diagnostic apparatus 10 includes a scanner 11 and an image processing device 12. The scanner 11 of the medical image diagnostic apparatus 10 is normally installed in an examination room, and generates X-ray transmission data on an object O. The image processing device 12 is normally installed in an operation room adjacent to the examination room, and generates projection data from the transmission data to generate and display a reconstruction image.

The scanner 11 of the medical image diagnostic apparatus 10 includes an X-ray tube 21, a collimator 22, an X-ray detector 23, a data acquisition system (DAS) 24, a rotor 25, a high-voltage power supply 26, a collimator driving apparatus 27, and a rotation driving apparatus 28 that are provided to a gantry 20. The scanner 11 further includes a bed 29, a top plate 30, a top plate driving apparatus 31, and a controller 32.

Voltage (hereinafter, referred to as tube voltage) is applied to the X-ray tube 21 by the high-voltage power supply 26, whereby the X-ray tube 21 generates an X-ray. The X-ray generated by the X-ray tube 21 is radiated as a fan beam X-ray or a cone beam X-ray toward the object O.

The collimator 22 is controlled by the controller 32 via the collimator driving apparatus 27 to adjust a radiation range in a slice direction, of the X-ray radiated from the X-ray tube 21.

The X-ray detector 23 is configured using one or more X-ray detecting elements (charge accumulating elements). Each X-ray detecting element detects the X-ray radiated from the X-ray tube 21. The X-ray tube 21 and the X-ray detector 23 are supported by the rotor 25 so as to be opposed to each other with the object O placed on the top plate 30 being interposed therebetween.

For example, a so-called one-dimensional array (single-slice) detector in which X-ray detecting elements having a plurality of channels in a channel (CH) direction are arranged in one line in the slice direction can be used as the X-ray detector 23. A so-called two-dimensional array (multi-slice) detector in which X-ray detecting elements having a plurality of channels in the channel (CH) direction are arranged in a plurality of lines in the slice direction can also be used as the X-ray detector 23. In a case of the multi-slice detector, X-ray detecting elements having a plurality of channels in the channel direction (X-axis) are arranged in a plurality of lines in the slice direction (Z-axis). Moreover, in a case of the two-dimensional array detector, the X-ray detector 23 can be configured using a plurality of X-ray detecting elements densely distributed and arranged in both the channel direction (X-axis) and the slice direction (Z-axis).

The DAS 24 amplifies signals of transmission data detected by the X-ray detecting elements constituting the X-ray detector 23, converts the signals into digital signals, and outputs the signals. The output data from the DAS 24 is given to the image processing device 12 via the controller 32 of the scanner 11.

The rotor 25 integrally holds the X-ray tube 21, the collimator 22, the X-ray detector 23, and the DAS 24, and is supported by the gantry 20. The rotor 25 is controlled by the controller 32 via the rotation driving apparatus 28 to rotate, whereby the X-ray tube 21, the collimator 22, the X-ray detector 23, and the DAS 24 integrally rotate around the object O. The rotor 25 is tiltable with respect to the gantry 20. Information on a current rotation speed, a tilting action, and information on a current tilt angle of the rotor 25 are given to the image processing device 12 via the rotation driving apparatus 28 and the controller 32.

The high-voltage power supply 26 is controlled by the controller 32 to supply electric power necessary for X-ray radiation to the X-ray tube 21.

The collimator driving apparatus 27 is controlled by the controller 32 to adjust an aperture of the collimator 22 and thus adjust the X-ray radiation range in the slice direction.

The rotation driving apparatus 28 is controlled by the controller 32 to rotate the rotor 25 around a hollow space.

The bed 29 is placed on a floor surface, and includes the top plate 30 for placing the object O and the top plate driving apparatus 31.

The object O can be placed on the top plate 30. The top plate driving apparatus 31 is controlled by the controller 32 to move the top plate 30 upward/downward in a Y-axis direction. The top plate driving apparatus 31 is controlled by the controller 32 to transport the top plate 30 to an X-ray radiation field in an opening portion of a central portion of the rotor 25 along the Z-axis direction. The top plate driving apparatus 31 is controlled by the controller 32 to move the top plate 30 along the X-axis direction (a short-axis direction of the top plate 30). The top plate 30 may be linearly moved from a movement start position to a movement destination position irrespective of the X-axis, Y-axis, and Z-axis directions. The top plate driving apparatus 31 can be controlled by the controller 32 to slew the top plate 30 about each of the X-axis, Y-axis, and Z-axis directions. Information on movement (a movement speed and a movement direction) and information on a current position of the top plate 30 are given to the image processing device 12 via the top plate driving apparatus 31 and the controller 32.

The controller 32 includes at least a processor, is configured using, for example, memory circuitry typified by the processor, a RAM, and a ROM, and controls the X-ray detector 23, the DAS 24, the high-voltage power supply 26, the collimator driving apparatus 27, the rotation driving apparatus 28, and the top plate driving apparatus 31 to execute scanning, in accordance with programs stored in the memory circuitry. The RAM of the controller 32 provides a work area for temporarily storing programs and data executed by the processor. The memory circuitry typified by the ROM of the controller 32 stores an activation program of the scanner 11, a control program of the scanner 11, and various pieces of data necessary to execute these programs.

The memory circuitry typified by the ROM of the controller 32 may include memory circuitry readable by the processor, such as a magnetic or optical recording medium or a semiconductor memory, and the entirety or a part of the programs and the data in the memory circuitry may be downloaded via an electronic network.

Meanwhile, the image processing device 12 of the medical image diagnostic apparatus 10 is configured using, for example, a personal computer, and can transmit/receive data to/from a network such as a hospital backbone local area network (LAN).

As illustrated in FIG. 1, the image processing device 12 includes an input circuit 41, a display 42, a network connection circuit 43, memory circuitry 44, and processing circuitry 45.

The input circuit 41 is configured using, for example, general input apparatuses such as a keyboard, a trackball, a touch panel, and a numeric keypad, and outputs an operation input signal corresponding to an operation by a user, to the processing circuitry 45. For example, if the user sets a scan plan (X-ray exposure plan) via the input circuit 41, the processing circuitry 45 gives the controller 32 an instruction for specifying, for example, X-ray exposure timing, an X-ray exposure period, and tube current and tube voltage to be applied to the X-ray tube 21, on the basis of the scan plan. The controller 32 instructs the high-voltage power supply 26 to supply electric power to the X-ray tube 21 using the tube current and the tube voltage specified by the processing circuitry 45, at the exposure timing and in the exposure period specified by the processing circuitry 45.

The input circuit 41 receives an instruction to tilt the rotor 25, an instruction to move the top plate 30, an instruction to change X-ray exposure conditions, and other instructions from the user.

The display 42 is configured using, for example, general display/output apparatuses such as a liquid crystal display and an organic light emitting diode (OLED) display, and displays various images such as a reconstruction image in accordance with control of the processing circuitry 45.

Various protocols for information communication respectively corresponding to network forms are implemented on the network connection circuit 43. The network connection circuit 43 connects the image processing device 12 to other electrical equipment such as an image server, in accordance with the various protocols. For example, electrical connection via an electronic network can be applied to this connection. The image server is, for example, a server for long-term image storage provided to a picture archiving and communication system (PACS), and stores image data and reconstruction images generated by modalities such as an X-ray computed tomography (CT) apparatus, an X-ray diagnostic apparatus, a nuclear medicine diagnostic apparatus, an ultrasonic diagnostic apparatus, and a magnetic resonance imaging (MRI) apparatus that are connected via a network.

The electronic network means overall information and communication networks using telecommunication technology, and includes a telephone communication network, an optical fiber communication network, a cable communication network, and a satellite communication network as well as wireless/wired LAN such as a hospital backbone LAN and the Internet.

The memory circuitry 44 includes memory circuitry readable/writable by a processor of the processing circuitry 45, such as a magnetic or optical recording medium or a semiconductor memory. The memory circuitry 44 stores pure raw data (projection data) and raw data (data obtained by preprocessing pure raw data using calibration data) that are collected by the scanner 11.

The processing circuitry 45 includes at least the processor. For instance, the processing circuitry 45 includes processor, and memory circuitry typified by a RAM and a ROM, and controls the controller 32 of the scanner 11 in accordance with a rotation speed controlling program stored in the memory circuitry.

The processor of the processing circuitry 45 loads, onto the RAM, the rotation speed controlling program and data necessary to execute this program, which are stored in the memory circuitry typified by the ROM, and executes a process for reducing electric power consumed in a scan waiting time and regaining a rotation speed of the imaging system in a short time, in accordance with this program.

The RAM of the processing circuitry 45 provides a work area for temporarily storing programs and data executed by the processor. The memory circuitry typified by the ROM of the processing circuitry 45 stores an activation program of the image processing device 12, the rotation speed controlling program, and various pieces of data necessary to execute these programs.

The memory circuitry typified by the ROM may include memory circuitry readable by the processor, such as a magnetic or optical recording medium or a semiconductor memory, and the entirety or a part of the programs and the data in the memory circuitry may be downloaded via an electronic network.

Figure 2:
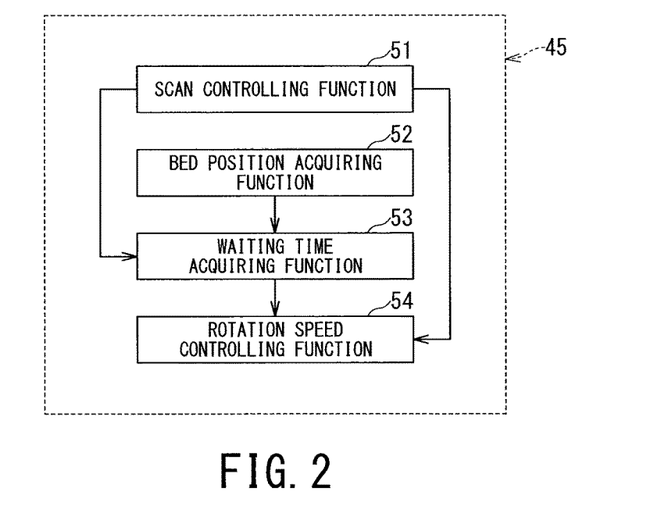
FIG. 2 is a schematic block diagram illustrating a function example implemented by the processor of the processing circuitry according to the present embodiment.

FIG. 2 is a schematic block diagram illustrating a function example implemented by the processor of the processing circuitry 45 according to the present embodiment.

As illustrated in FIG. 2, the rotation speed controlling program causes the processor of the processing circuitry 45 to function as at least a scan controlling function 51, a bed position acquiring function 52, a waiting time acquiring function 53, and a rotation speed controlling function 54. These functions are each stored in the memory circuitry in the form of a program.

The scan controlling function 51 receives an instruction to execute an X-ray exposure plan (scan plan) from the user via the input circuit 41, and controls the scanner 11 via the controller 32 on the basis of this plan, to thereby rotate the X-ray tube 21 and the X-ray detector 23 around the object O and collect projection data. The processing circuitry 45 can generate a reconstruction image on the basis of the projection data, and can display the reconstruction image on the display 42.

The bed position acquiring function 52 acquires information on movement (a movement speed and a movement direction) and information on a current position of the top plate 30 on which the object O is placed, via the top plate driving apparatus 31 and the controller 32.

The waiting time acquiring function 53 acquires information on a waiting time T (scan waiting time) up to next exposure timing. For example, the waiting time acquiring function 53 may acquire the information on the waiting time T from a currently executed X-ray exposure plan, and may estimate the waiting time T from a current status of the medical image diagnostic apparatus 10 such as a retraction state of the top plate 30 and the time elapsed from an end of an X-ray exposure plan.

In a case where the waiting time T (scan waiting time) up to the next exposure timing is long, a rotation speed of the rotor 25 may be made lower such that electric power consumed in the waiting time T is reduced and that the rotation speed of the imaging system is regained in a short time. Even if the rotation speed of the rotor 25 is made lower, if a period of time sufficient for reacceleration up to a rotation speed required for the next exposure can be secured by the next exposure timing, execution of the next X-ray exposure plan is not hindered.

In view of this, in a period up to next exposure by the X-ray tube 21, the rotation speed controlling function 54 controls a rotation speed v of the rotor 25 such that the rotor 25 rotates at a rotation speed lower than a rotation speed required for the next exposure by the X-ray tube 21. More specifically, the rotation speed controlling function 54 controls the rotation speed of the rotor 25, for example, such that the rotation speed thereof reaches the required rotation speed by the time of the next exposure by the X-ray tube 21 and that an average rotation speed thereof is lowest in a period (waiting time T) from the present moment up to the next exposure. Moreover, in a case of accelerating and decelerating the rotation speed of the rotor 25 in a stepwise manner, the rotation speed controlling function 54 may control the rotation speed thereof such that an average of respective rotation speeds of stages is lowest in the period (waiting time T) from the present moment up to the next exposure.

The rotation speed controlling function 54 can cause the rotor 25 to keep rotating at a low speed, in order to avoid rotation stop of the rotor 25. In this case, the time required to start rotations of the rotor 25 in a rotation stop state can be omitted. In general, an enormous amount of energy and time is required to restart rotations of a heavy object such as the rotor 25 from a rotation stop state. Hence, in a case of such control that avoids rotation stop, the time required for rotation restart is unnecessary compared with control that allows a rotation stop state, and hence the time required to regain the rotation speed of the rotor 25 can be considerably shortened.

Figure 3:
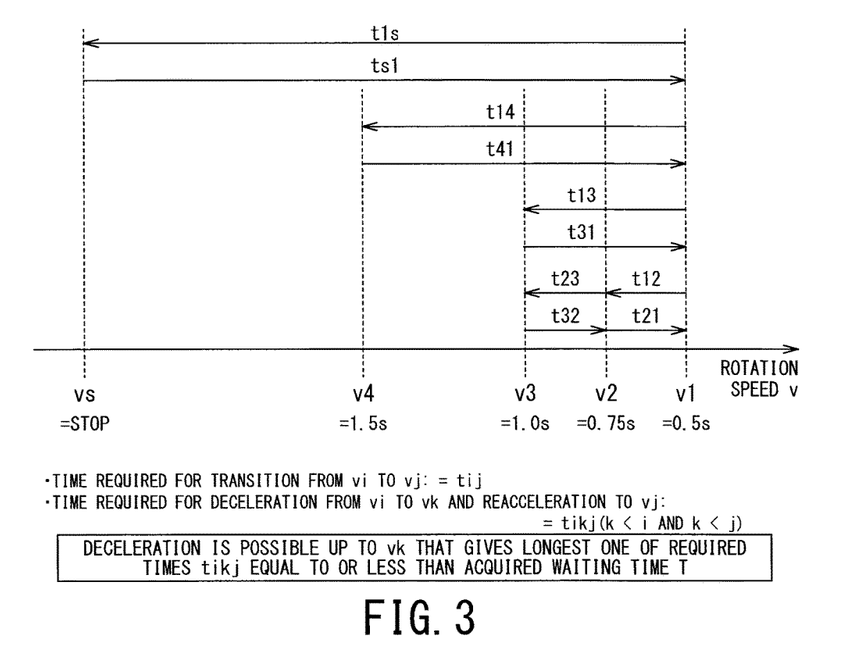
FIG. 3 is an explanatory view illustrating an example of the time required for transition among a plurality of rotation speeds of the rotor.

FIG. 3 is an explanatory view illustrating an example of the time required for transition among a plurality of rotation speeds of the rotor 25. FIG. 3 illustrates an example case where v1 is 0.5 seconds/rotation, v2 is 0.75 seconds/rotation, and the like, but a rotation speed possible for the rotor 25 is not limited to numerical values illustrated in FIG. 3.

The rotor 25 is controlled by the rotation speed controlling function 54 via the rotation driving apparatus 28 and the controller 32 to rotate at, for example, any of the plurality of rotation speeds as illustrated in FIG. 3. It is assumed that the time required for transition from a rotation speed v1 to a rotation speed vj is tij. It is also assumed that the time required for deceleration from the rotation speed v1 to a rotation speed vk and reacceleration to the rotation speed vj is tikj (where k<i and k<j).

In this case, when the current rotation speed v1 and the rotation speed vj required for next exposure are given, if there are required times tikj equal to or less than the waiting time T, deceleration is regarded as possible up to the rotation speed vk that gives the longest one of these required times tikj.

On the other hand, if a length of the period up to the next exposure is less than a predetermined length, the rotation speed controlling function 54 may control the rotation speed v of the rotor 25 to maintain the current rotation speed v1. For example, a case where there is no required time tikj equal to or less than the waiting time T means that the rotation speed cannot return to the required rotation speed vj by the next exposure timing. In this case, deceleration may hinder smooth execution of an X-ray exposure plan, and hence it is preferable to maintain the current rotation speed v1 without deceleration. In this case, the rotation speed controlling function 54 may control the rotor 25 to maintain the current rotation speed v1.

In a case where information on a maximum acceleration rate (hereinafter, referred to as an allowable maximum acceleration rate) that can be given to the rotor 25 can be obtained, the rotation speed controlling function 54 may accelerate the rotation speed of the rotor 25 using a predetermined acceleration rate within a range of the allowable maximum acceleration rate. The allowable maximum acceleration rate is determined by strength of hardware concerning rotations of the medical image diagnostic apparatus 10 (for example, the gantry and members such as a bearing of the X-ray tube 21 held and rotated by the rotor 25), a rotation driving capability of the rotation driving apparatus 28, software, and the like. Information on the allowable maximum acceleration rate may be stored in advance in the memory circuitry 44, and may be given by the user via the input circuit 41.

In this case, for example, the rotation speed controlling function 54 causes the rotor 25 to keep rotating at a low rotation speed, up to a moment that is earlier by a required acceleration period than the timing of the exposure by the X-ray tube 21, the required acceleration period being obtained in accordance with a predetermined acceleration rate within the range of the allowable maximum acceleration rate, that is, up to a last moment at which the required rotation speed can be reached by acceleration using the predetermined acceleration rate within the range of the allowable maximum acceleration rate. The required acceleration period can be obtained from: a difference between the rotation speed required for the exposure and the low rotation speed; and the predetermined acceleration rate used for the acceleration. The acceleration rate used for the acceleration may be equal to or lower than the allowable maximum acceleration rate.

The acceleration rate may not be constant in the acceleration period, and may change in a stepwise manner, for example. In a case where the acceleration rate is not constant in the acceleration period, "the predetermined acceleration rate used for the acceleration" can be translated as an average acceleration rate in the acceleration period. As the predetermined acceleration rate becomes closer to the allowable maximum acceleration rate, the rotation speed can be more quickly regained.

The rotation speed controlling function 54 accelerates the rotation speed of the rotor 25 using the predetermined acceleration rate within the range of the allowable maximum acceleration rate, from the moment that is earlier by the required acceleration period than the exposure timing, whereby the rotation speed controlling function 54 enables the rotation speed of the rotor 25 to reach the required rotation speed at the timing of the exposure by the X-ray tube 21.

In this way, in a case of performing the acceleration using the predetermined acceleration rate within the range of the allowable maximum acceleration rate, the acceleration period required before the rotation speed required for the exposure is reached can be made shortest. Accordingly, in this case, because a period in which the rotor 25 rotates at a low speed can be lengthened, consumed electric power can be further reduced.

Figure 4:
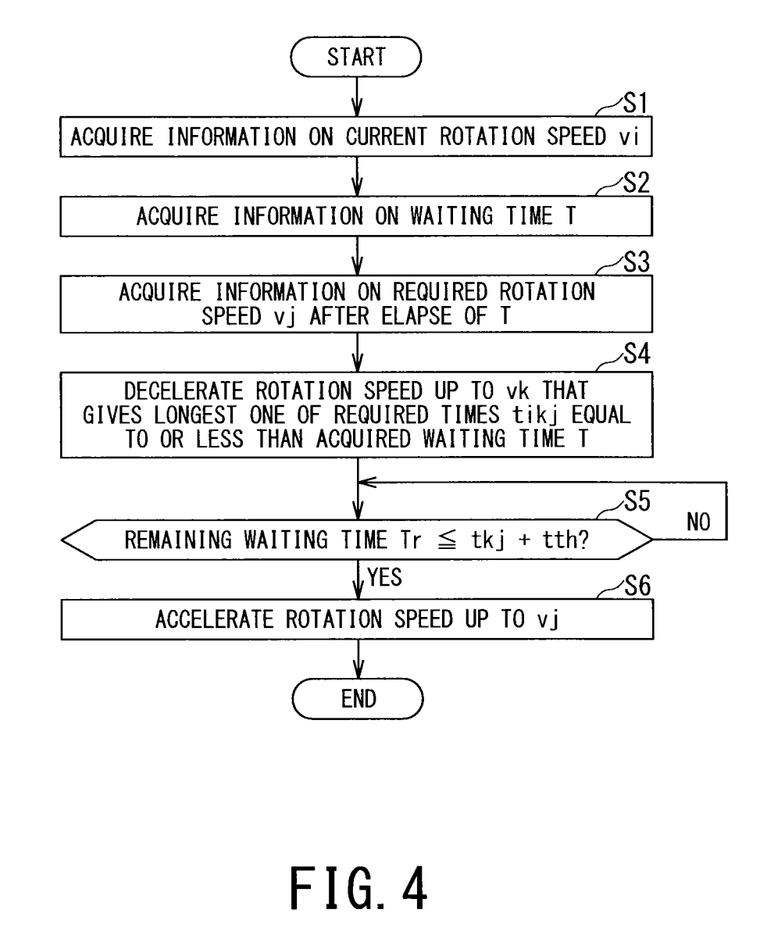
FIG. 4 is a flowchart illustrating an example procedure performed when the processor of the image processing device illustrated in FIG. 1 reduces electric power consumed in a scan waiting time, and regains the rotation speed of the imaging system in a short time.

FIG. 4 is a flowchart illustrating an example procedure performed when the processor of the image processing device 12 illustrated in FIG. 1 reduces electric power consumed in a scan waiting time, and regains the rotation speed of the imaging system in a short time. In FIG. 4, reference signs of S with a number respectively denote steps in the flowchart.

First, in Step S1, the rotation speed controlling function 54 acquires information on the current rotation speed v1 of the rotor 25 via the rotation driving apparatus 28 and the controller 32.

In Step S2, the waiting time acquiring function 53 acquires information on the waiting time T up to next exposure timing.

In Step S3, the rotation speed controlling function 54 acquires information on the required rotation speed vj to be reached after an elapse of the waiting time T. In a case where an X-ray exposure plan is set, the information on the required rotation speed vj can be acquired from the plan. In a case where an X-ray exposure plan is not set, a speed equal to the current rotation speed v1 may be set as vj.

In Step S4, the rotation speed controlling function 54 decelerates the rotation speed up to the rotation speed vk that gives the longest one of the required times tikj equal to or less than the waiting time T. In a case where there is no required time tikj equal to or less than the waiting time T, the procedure is ended with the rotation speed being maintained.

In Step S5, it is determined whether or not a remaining waiting time Tr is equal to or less than a value obtained by adding a predetermined threshold tth to tkj (the time required for transition from the rotation speed vk to the rotation speed vj). If Tr is more than tkj+tth, there is no problem even if the low-speed rotations are continued, and hence Step S5 is repeated. On the other hand, if Tr is equal to or less than tkj+tth, the procedure goes to Step S6.

In Step S6, the rotation speed controlling function 54 controls the rotor 25 via the rotation driving apparatus 28 and the controller 32 to accelerate the rotation speed of the rotor 25 up to the rotation speed vj.

Through the above-mentioned procedure, the electric power consumed in the scan waiting time can be reduced, and the rotation speed of the imaging system can be regained in a short time. At this time, such control that does not hinder execution of the X-ray exposure plan is possible.

Next, specific examples of using the medical image diagnostic apparatus 10 are described.

(Exposure Waiting Time at the Time of Executing Contrast X-Ray Exposure Plan)

Figure 5:
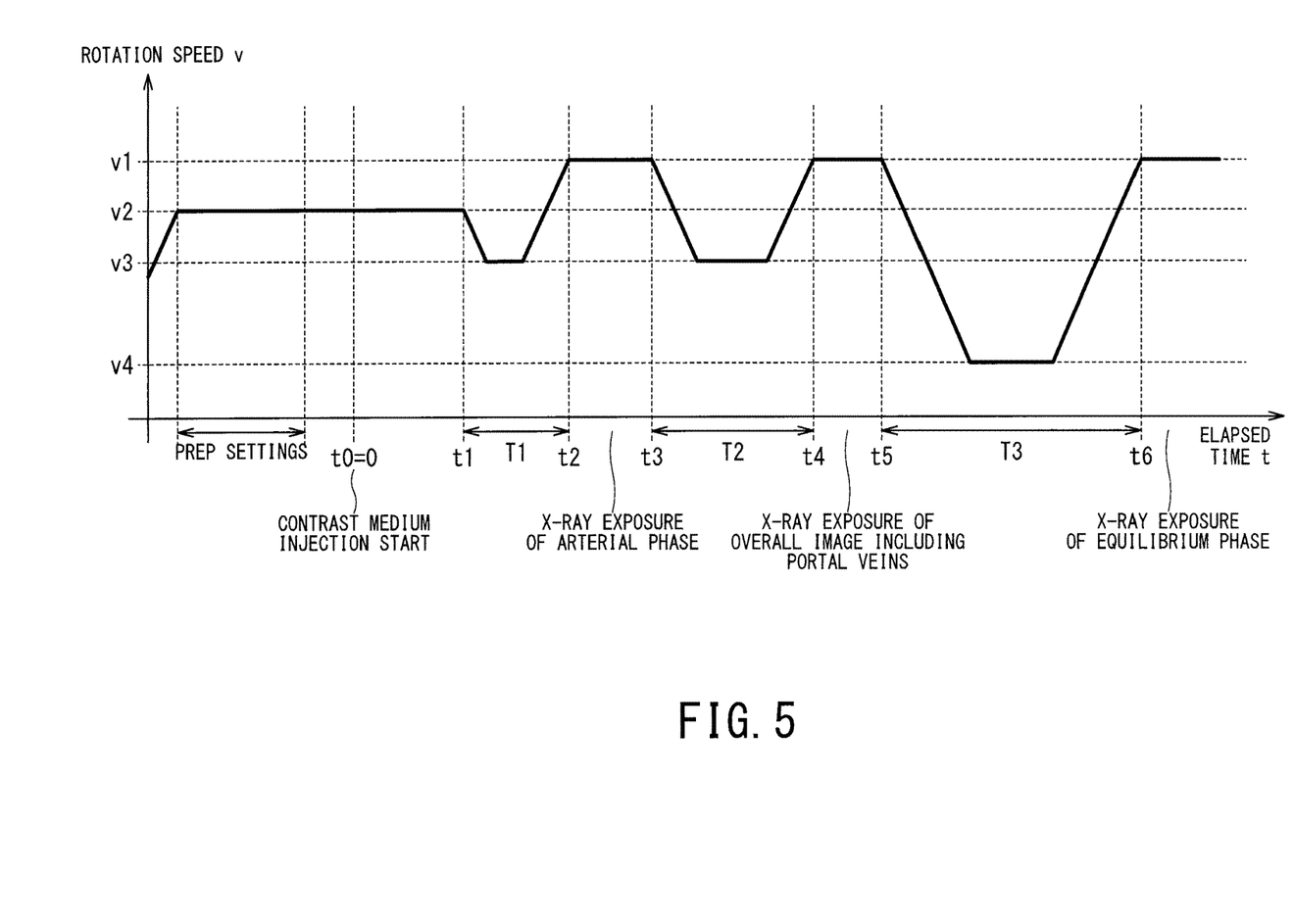
FIG. 5 is an explanatory view illustrating an example state where the rotation speed controlling function controls the rotation speed v of the rotor when abdominal contrast radiography using a bolus tracking method as a contrast X-ray exposure plan is performed.

FIG. 5 is an explanatory view illustrating an example state where the rotation speed controlling function 54 controls the rotation speed v of the rotor 25 when abdominal contrast radiography using a bolus tracking method as a contrast X-ray exposure plan is performed.

The abdominal contrast radiography using the bolus tracking method is performed according to, for example, the following procedure.

First, after scanography for rough positioning is performed, plain X-ray exposure for positioning is performed. Then, after prep settings are made, a contrast medium is injected at a time t0=0. In the prep settings, a rotation speed equivalent to that in real scanning does not necessarily need to be adopted, and FIG. 5 illustrates an example case where a required rotation speed in the real scanning is v1 whereas a required rotation speed in the prep settings is v2.

At t=t1, if it is automatically detected that a concentration of the contrast medium within a predetermined region of interest becomes equal to or more than a predetermined concentration, movement of the top plate 30 is started, and the object O is automatically moved to an imaging start position, in order to perform imaging of an arterial phase. At t=t2 (for example, t2=about 30 seconds to 40 seconds), X-ray exposure of the arterial phase is automatically started. At this time, a waiting time T1 from t=t1 to t=t2 occurs during the movement of the top plate 30. The waiting time acquiring function 53 acquires the waiting time T1 from design values of a movement distance of the top plate 30 and a movement speed of the top plate 30 included in the plan. Alternatively, the waiting time acquiring function 53 may estimate the waiting time T1 by, for example, detecting that the movement of the top plate 30 is started. The rotation speed controlling function 54 compares T1 with t2k1. If there are required times t2k1 equal to or less than T1, the rotation speed controlling function 54 decelerates the rotation speed v of the rotor 25 up to the rotation speed vk that gives the longest one of these required times t2k1. FIG. 5 illustrates an example case where the rotation speed v of the rotor 25 is decelerated up to v3.

At t=t3, the imaging of the arterial phase is ended. Then, at t=t4 (for example, t4=about 70 seconds to 80 seconds), X-ray exposure of an overall image including portal veins is automatically started. At this time, a waiting time T2 from t3 to t4 occurs. Also in the waiting time T2, similarly to T1, the rotation speed controlling function 54 provides a period in which the rotor 25 rotates at a rotation speed lower than v1.

At t=t5, the X-ray exposure of the overall image including the portal veins is ended. Then, at t=t6 (for example, t6=about 3 minutes), X-ray exposure of an equilibrium phase is automatically started. At this time, a waiting time T3 from t5 to t6 occurs. Also in the waiting time T3, similarly to T1 and T2, the rotation speed controlling function 54 provides a period in which the rotor 25 rotates at a rotation speed lower than v1.

In this way, according to the medical image diagnostic apparatus 10, rotation deceleration and rotation stop of the rotor 25 can be automatically controlled in accordance with the exposure waiting time that occurs at the time of executing the contrast X-ray exposure plan.

(Exposure Waiting Time Due to Restriction on Heat Capacity of X-Ray Tube 21)

The X-ray tube 21 may be provided with a tube protecting function for preventing a breakdown due to an overload put by heat accumulated by X-ray generation. In this case, the tube protecting function is used to prevent heat accumulated in the X-ray tube 21 from exceeding a predetermined range, on the basis of an amount of heat generation by the X-ray tube 21 and a cooling efficiency of a cooling apparatus (not illustrated) for cooling the X-ray tube 21. The amount of heat generation by the X-ray tube 21 changes in accordance with X-ray generation conditions (tube voltage, tube current, a focal point, and X-ray generation time).

In a case where a waiting time T due to a restriction on a heat capacity of the X-ray tube 21 occurs during X-ray exposure by means of the tube protecting function, information on the waiting time T is given from the controller 32 to the image processing device 12. In this case, the waiting time acquiring function 53 acquires the information on the waiting time T, and gives the information to the rotation speed controlling function 54. The rotation speed controlling function 54 controls the rotation speed of the rotor 25 in accordance with the waiting time T.

In a case where the user changes the X-ray generation conditions via the input circuit 41, the rotation speed controlling function 54 may decelerate the rotation speed of the rotor 25 by one stage during the operation by the user. In this case, as soon as the user gives an instruction to restart radiography, the rotation speed controlling function 54 accelerates the rotation speed of the rotor 25 by one stage to the previous speed, and stands by for the radiography.

Note that, after a contrast examination, in a case where a waiting time due to the restriction on the heat capacity of the X-ray tube 21 occurs at the time of additional radiography, a state where the additional radiography is possible may be maintained without performing deceleration control.

In this way, according to the medical image diagnostic apparatus 10, in a case where the waiting time T up to X-ray exposure occurs due to the restriction on the heat capacity of the X-ray tube 21, rotation deceleration and rotation stop of the rotor 25 can be automatically controlled in accordance with the waiting time.

(Waiting Time Due to Amount of Movement of Top Plate 30 after End of Exposure)

Figure 6:
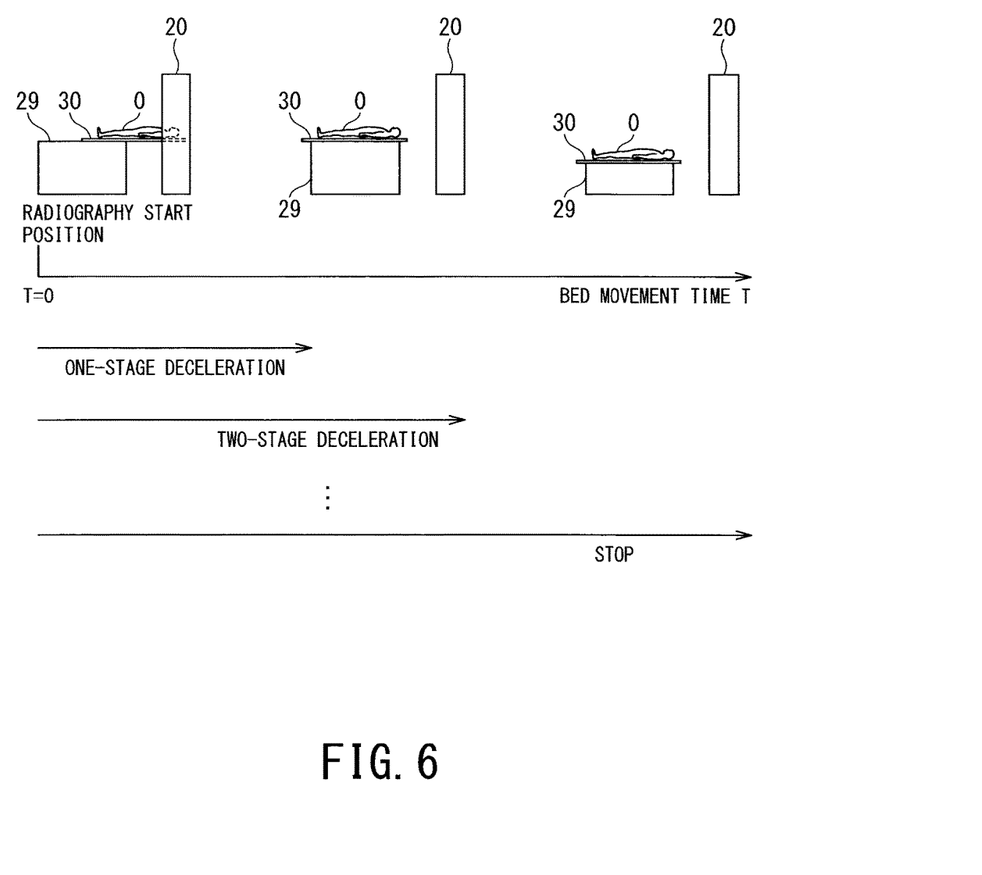
FIG. 6 is an explanatory view illustrating an example state where the waiting time T is estimated in accordance with an amount of movement of the top plate.

FIG. 6 is an explanatory view illustrating an example state where the waiting time T is estimated in accordance with an amount of movement of the top plate 30.

After an end of X-ray exposure, there can be cases where entire radiography work is ended and exposure is not to be performed thereafter and where some work still remains and next exposure is to be performed. Hence, only because the X-ray exposure is ended, if rotations of the rotor 25 are uniformly stopped, a waiting time only for rotation acceleration of the rotor 25 unfavorably occurs when the need to perform the next exposure arises, so that an enormous amount of stress is put on the user and the object O.

In view of this, the medical image diagnostic apparatus 10 according to the present embodiment changes the rotation speed of the rotor 25 in a stepwise manner in accordance with the amount of movement of the top plate 30.

Specifically, the bed position acquiring function 52 acquires a radiography position of the top plate 30 when the X-ray exposure is ended and a current position of the top plate 30. The waiting time acquiring function 53 estimates, as the waiting time T, the time necessary for the top plate 30 to return from the current position to the radiography position when the X-ray exposure is ended. The waiting time T is equal to the time that is required at the present moment to return to a previous radiography position when the user gives an instruction to perform radiography.

The top plate 30 may be moved along the X-axis direction, may be moved along the Y-axis direction, may be moved along the Z-axis direction, may be slewed about each of the X-axis, Y-axis, and Z-axis directions, may be moved in a stepwise manner according to a combination of these movements, or may be linearly moved from a movement start position to a movement destination position irrespective of the X-axis, Y-axis, and Z-axis directions. For example, in a case where the top plate 30 is moved in a stepwise manner, the waiting time acquiring function 53 estimates the waiting time T considering the stepwise movement.

For example, FIG. 6 illustrates an example case where the top plate 30 is moved farther from a radiography position according to a stepwise movement, in which the top plate 30 is moved along the Z-axis direction and then moved along the Y-axis direction. In such a case where the top plate 30 is monotonously moved farther from the radiography position, the rotation speed controlling function 54 decelerates the rotation speed of the rotor 25 stage by stage (see FIG. 6).

In this way, according to the medical image diagnostic apparatus 10, the waiting time T is estimated in accordance with the amount of movement of the top plate 30 from the radiography position after the X-ray exposure is ended, and rotation deceleration and rotation stop of the rotor 25 can be automatically controlled in accordance with the waiting time.

Hence, in spite of a case where entire work is ended and exposure is not to be performed thereafter, even if the user forgets to stop rotations of the rotor 25 or prioritizes retraction of the object O and moves the top plate 30, the rotation speed of the rotor 25 can be decelerated stage by stage in a stepwise manner. Moreover, in a case where a purpose of moving the top plate 30 is position adjustment of the object O or the like and where radiography is to be restarted, the rotation speed controlling function 54 can easily and reliably return the rotation speed of the rotor 25 up to a rotation speed required for the previous exposure, by the time the top plate 30 is returned to the previous radiography position. Accordingly, even in the case where the radiography is to be restarted, a waiting time for rotation acceleration of the rotor 25 does not occur, and hence unnecessary stress is not put on the user and the object O, which is extremely advantageous.

(Waiting Time after End of X-Ray Exposure Plan)

Also after an X-ray exposure plan is ended, similarly to the above-mentioned case where the top plate 30 is moved after the X-ray exposure is ended, there can be cases where entire radiography work is ended and exposure is not to be performed thereafter and where some work still remains and next exposure is to be performed. In a case where the top plate 30 is not particularly moved, a simple end of the X-ray exposure plan leaves open a possibility that radiography is restarted immediately after the plan is changed or modified.

In view of this, information on a shortest time T required for a plan change may be stored in advance in the memory circuitry 44, and the information on the shortest time T may be first used as the information on the waiting time T. Instead of using the shortest time T, one-stage deceleration may be first performed after a radiography plan is ended. After that, the rotation speed controlling function 54 may decelerate the rotation speed of the rotor 25 in a stepwise manner in accordance with the time elapsed from the end of the radiography plan. This is because, as the time elapsed from the end of the radiography plan becomes longer, a possibility that entire radiography work is ended and exposure is not to be performed thereafter becomes higher. At a moment at which the elapsed time exceeds a predetermined time (for example, 3 minutes), rotations of the rotor 25 may be stopped.

In this way, according to the medical image diagnostic apparatus 10, rotations of the rotor 25 are not stopped immediately after the X-ray exposure plan is ended, and the rotation speed of the rotor 25 can be decelerated in a stepwise manner in accordance with the time elapsed from the end of the radiography plan.

In this case, in a case where radiography may be immediately restarted (such as a case where the ended X-ray exposure plan is a plan concerning a contrast examination), deceleration may not be performed in a predetermined time.

(Waiting Time Due to Operation on Top Plate and Gantry by User)

In a case where movement of at least one of the top plate 30 and the gantry 20 is started by an instruction that is given by the user via the input circuit 41, it is easily expected that a certain amount of waiting time up to next X-ray exposure exists.

For example, discussed is a case where a plan in which a pause period is set after scanography and plain X-ray exposure and before radiography start is selected as an X-ray exposure plan. In this case, it is expected that, during the pause period, for example, the user sets a target site as a center of the radiography, and moves at least one of the top plate 30 and the gantry 20 such that the set target site is located in the center of the radiography.

In view of this, information on a shortest time T required after the scanography and the plain X-ray exposure and before the radiography start may be stored in advance in the memory circuitry 44, and the information on the shortest time T may be first used as the information on the waiting time T. Instead of using the shortest time T, in a case where a movement operation on at least one of the top plate 30 and the gantry 20 is received from the user after the scanography and the plain X-ray exposure, the rotation speed controlling function 54 may first decelerate the rotation speed of the rotor 25 by one stage. After that, a movement time of each of the top plate 30 and the gantry 20 is obtained on the basis of the movement operation by the user, and the rotation speed of the rotor 25 is controlled in accordance with the movement time used as the waiting time T.

In this way, according to the medical image diagnostic apparatus 10, rotation deceleration and rotation stop of the rotor 25 can be automatically controlled in accordance with the waiting time that occurs in the case where the movement operation on at least one of the top plate 30 and the gantry 20 is received from the user.

(Case where Plan for which Preparations Take Time is Selected)

In a case where a plan that requires at least one of utilization of a contrast medium, utilization of a large intestine injector, electrocardiographic synchronization, and respiratory synchronization is selected, a preparation time is necessary before real scanning is executed. Accordingly, the preparation time is used as the waiting time T, and the rotation speed of the rotor 25 may be controlled in accordance with the preparation time.

For example, in a case where a plan that requires electrocardiographic synchronization and respiratory synchronization is selected, scanography and plain X-ray exposure are first performed, and preliminary scanning is then performed. Then, the time for heart rate acquisition and the time for respiration training are consumed before the real scanning, and the real scanning is finally started.

In view of this, information on an estimated time T of each of the time for heart rate acquisition and the time for respiration training may be stored in advance in the memory circuitry 44, and the information on the estimated time T may be used as the information on the waiting time. Instead of using the estimated time T, the rotation speed of the rotor 25 may be decelerated by one stage.

A period between: the scanography and the plain X-ray exposure; and the preliminary scanning may be treated as a waiting time, and rotations of the rotor 25 may be accelerated and decelerated also in this period.

For example, in a case where a plan that requires utilization of an injector is selected, an injection pressure of a contrast medium may abnormally rise. This can occur in a case where a needle of the injector is not properly inserted into a blood vessel and where the contrast medium leaks, for example. In such a case, an examination is normally interrupted. In a case where the examination is interrupted, a waiting time occurs, and hence rotations of the rotor 25 may be decelerated. Accordingly, for example, in a case where it is determined on the basis of a signal from the contrast medium injector that the injection pressure of the contrast medium rises to a threshold or higher, the rotation speed controlling function 54 decelerates the rotation speed of the rotor 25.

(Waiting Time from Radiography Start Operation Input to X-Ray Exposure)

In a period after the user presses a radiography button (a so-called confirmation button) and before X-ray exposure is really performed at a required rotation speed, there is a time in which: the top plate 30 is automatically moved; and a radiography target site is about to enter a radiography region from an outside of the radiography region. Because it is sufficient that the rotation speed of the rotor 25 reaches the required rotation speed at a moment at which the radiography target site is about to enter the radiography region, a period in which the radiography target site is outside of the radiography region can be used as a rotation acceleration time.

In view of this, the period after the user presses the radiography button and before the X-ray exposure is really performed is treated as a waiting time, and the rotation speed of the rotor 25 is controlled in this period. For example, in a case where the waiting time is 10 seconds and where radiography is performed at 0.275 seconds/rotation, the rotation speed of the rotor 25 is decelerated up to 0.3 seconds/rotation.

In the medical image diagnostic apparatus 10 according to the present embodiment, as described above, a period for reducing the rotation speed of the rotor 25 is provided even in a seemingly small amount of waiting time through automatic control without reception of a manual operation by the user, whereby electric power consumed in a scan waiting time can be reduced and the rotation speed of the imaging system can be regained in a short time. Consequently, a load on members such as the bearing of the X-ray tube 21 held and rotated by the rotor 25 can be reduced, and lifetimes of these members can be lengthened. Moreover, consumed electric power can be reduced compared with a case of maintaining the rotation speed of the rotor 25.

The medical image diagnostic apparatus 10 can cause the rotor 25 to keep rotating at a low speed, in order to avoid rotation stop of the rotor 25. In this case, compared with a case of restarting rotations from a rotation stop state, the time required to start rotations of the rotor 25 in a rotation stop state can be omitted, and hence the time required to regain the rotation speed of the rotor 25 can be considerably shortened.

The medical image diagnostic apparatus 10 can automatically control the rotation speed of the rotor 25, for example, such that the rotation speed thereof reaches a required rotation speed by the time of next exposure by the X-ray tube 21 and that an average rotation speed thereof is lowest in a period (waiting time T) from the present moment up to the next exposure. Hence, a period in which the rotor 25 rotates at an unnecessary rotation speed can be shortened as much as possible, without hindering execution of an X-ray exposure plan. Accordingly, a longer lifetime of the apparatus and smaller consumed electric power can be achieved without putting an unnecessary stress on the user and the object O.

With at least one of the above-described embodiments, a medical image diagnostic apparatus 10 can control the rotation speed of the rotor 25 in accordance with a scan waiting time, thereby reducing electric power consumed in the scan waiting time and regaining a rotation speed of the imaging system in a short time.

The processing circuitry in the above-described embodiments is an example of the processing circuitry described in the claims. In addition, the term "processor" used in the explanation in the above-described embodiments, for instance, a circuit such as a dedicated or general-purpose CPU (Central Processing Unit), a dedicated or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array). A processor implements various types of functions by reading out programs stored in the memory circuit and executing the programs.

In addition, programs may be directly installed in the circuit of a processor instead of storing programs in the memory circuit. In this case, the processor implements various types of functions by reading out programs stored in its own circuit and executing the programs. Moreover, each function of the processing circuitry may be implemented by processing circuitry configured of a single processor. Further, the processing circuitry may be configured by combining plural processors independent of each other so that each function of the processing circuitry is implemented by causing each processor to execute the corresponding program. When plural processors are provided for the processing circuitry, a memory circuit for storing the programs may be provided for each processor or one memory circuit may collectively store all the programs corresponding to all the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, in a case where there is enough time for start timing of real scanning in an X-ray exposure plan, the rotation speed controlling function 54 may instruct the scanner 11 to: accelerate the rotation speed of the rotor 25 up to a rotation speed required for the real scanning in the exposure plan; and start X-ray exposure according to the exposure plan when the rotation speed of the rotor 25 reaches the required rotation speed. In this case, as soon as the rotation speed of the rotor 25 reaches the required rotation speed, the real scanning can be executed. Hence, a period in which the rotor 25 rotates at a high rotation speed can be used without being wasted, and a period in which the rotor 25 rotates at an unnecessary rotation speed can be shortened.

The invention claimed is:

1. A medical image diagnostic apparatus, comprising:
an X-ray tube configured to radiate an X-ray;
a rotor configured to hold the X-ray tube and rotate together with the X-ray tube at least two predetermined, constant rotational speeds, including a first rotation speed used for scanning an object and a second, non-zero rotation speed lower than the first rotation speed; and
processing circuitry configured to
acquire information on a waiting time until a time of exposure by the X-ray tube, and
control a rotation speed of the rotor during the waiting time in accordance with the acquired information on the waiting time.

2. The medical image diagnostic apparatus according to claim 1, wherein the processing circuitry is further configured to acquire, as the information on the waiting time, information on an exposure waiting time that occurs at a time of executing a contrast X-ray exposure plan.

3. The medical image diagnostic apparatus according to claim 1, wherein the processing circuitry is further configured to acquire, as the information on the waiting time, information on a waiting time that occurs due to a restriction on a heat capacity of the X-ray tube.

4. The medical image diagnostic apparatus according to claim 1, wherein the processing circuitry is further configured to
acquire information on a current position of a top plate on which the object is placed, and
estimate the information on the waiting time in accordance with the current position of the top plate and a position of the top plate when exposure by the X-ray tube is ended.

5. The medical image diagnostic apparatus according to claim 1, wherein when an X-ray exposure plan is ended, the processing circuitry is configured to control the rotation speed of the rotor in accordance with a time elapsed from the end of the X-ray exposure plan.

6. The medical image diagnostic apparatus according to claim 1, wherein when movement of at least one of a top plate and the rotor is started by an instruction that is given by a user via an input circuit, the processing circuitry is configured to estimate the waiting time until the time of exposure by the X-ray tube that occurs due to the movement, and use information on the estimated waiting time as the information on the waiting time.

7. The medical image diagnostic apparatus according to claim 1, wherein when one of a plurality of X-ray exposure plans is selected to be started, the processing circuitry is configured to estimate the waiting time until the time of exposure by the X-ray tube, based on information on the selected plan, and use information on the estimated waiting time as the information on the waiting time.

8. The medical image diagnostic apparatus according to claim 7, wherein the X-ray exposure plan whose start is selected is a plan that requires at least one of utilization of a contrast medium, utilization of a large intestine injector, electrocardiographic synchronization, and respiratory synchronization.

9. The medical image diagnostic apparatus according to claim 1, wherein when an instruction to start X-ray radiography is given, the processing circuitry is configured to obtain a waiting time from a moment at which the instruction is given to the time of X-ray exposure, and use information on the obtained waiting time as the information on the waiting time.

10. The medical image diagnostic apparatus according to claim 1, wherein when a predetermined X-ray exposure plan is selected to be started, the processing circuitry is configured to instruct an imaging apparatus to accelerate the rotation speed of the rotor up to a rotation speed required for the predetermined X-ray exposure plan, and instruct the imaging apparatus to start X-ray exposure according to the predetermined X-ray exposure plan when the rotation speed of the rotor reaches the rotation speed required for the predetermined X-ray exposure plan.

11. The medical image diagnostic apparatus according to claim 1, wherein when a length of a period up to the exposure by the X-ray tube is less than a predetermined length, the processing circuitry is configured to control the rotation speed of the rotor to maintain a current rotation speed.

12. A medical image diagnostic apparatus, comprising:
a rotor configured to hold an X-ray tube and rotate together with the X-ray tube; and
processing circuitry configured to control a rotation speed of the rotor in a time period until exposure by the X-ray tube such that the rotor rotates at a first, non-zero rotation speed lower than a second rotation speed required for the exposure by the X-ray tube.

13. A medical image diagnostic method for a medical image diagnostic apparatus that includes an X-ray tube configured to radiate an X-ray, a rotor configured to hold the X-ray tube, and rotate together with the X-ray tube at least two predetermined, constant rotational speeds, including a first rotation speed used for scanning an object and a second, non-zero rotation speed lower than the first rotation speed, the medical image diagnostic method comprising:
acquiring information on a waiting time until a time of exposure by the X-ray tube; and
controlling a rotation speed of the rotor during the waiting time in accordance with the information on the waiting time.

14. The medical image diagnostic apparatus of claim 1, wherein the processing circuitry is further configured to control the rotation speed of the rotor during the waiting time to include a period during which the rotation speed of the rotor is set at a fixed, non-zero rotation speed other than the first rotation speed.

* * * * *